(12) United States Patent
Risi et al.

(10) Patent No.: US 9,597,503 B2
(45) Date of Patent: Mar. 21, 2017

(54) INTRA-COCHLEAR STIMULATING ASSEMBLY INSERTION

(71) Applicant: Cochlear Limited, Macquarie University, NSW (AU)

(72) Inventors: Frank Risi, Newtown (AU); Shaun Ashwin Kumar, Rockdale (AU); Andrea Lam, Ryde (AU); Paul Michael Carter, West Pennant Hills (AU)

(73) Assignee: Cochlear Limited, Macquarie University, NSW (AU)

( * ) Notice: Subject to any disclaimer, the term of this patent is extended or adjusted under 35 U.S.C. 154(b) by 0 days.

(21) Appl. No.: 14/843,259

(22) Filed: Sep. 2, 2015

(65) Prior Publication Data
US 2016/0059015 A1    Mar. 3, 2016

Related U.S. Application Data

(60) Provisional application No. 62/044,599, filed on Sep. 2, 2014.

(51) Int. Cl.
| A61N 1/00 | (2006.01) |
| A61N 1/36 | (2006.01) |
| A61N 1/05 | (2006.01) |

(52) U.S. Cl.
CPC ....... *A61N 1/36032* (2013.01); *A61N 1/0541* (2013.01)

(58) Field of Classification Search
CPC .......................... A61N 1/0541; A61N 1/36032
See application file for complete search history.

(56) References Cited

U.S. PATENT DOCUMENTS 6,070,105 A * 5/2000 Kuzma ................ A61N 1/0541
607/137
8,073,547 B2   12/2011 Hong et al.
(Continued)

FOREIGN PATENT DOCUMENTS

| EP | 0906713 B1 | 10/2004 |
| WO | 2012168921 A2 | 12/2012 |
| WO | 2013/152077 A1 | 10/2013 |

OTHER PUBLICATIONS

B. Escudé et al., "The Size of the Cochlea and Predictions of Insertion Depth Angles for Cochlear Implant Electrodes", Audiology & Neurotology, www.karger.com/aud, Audiol Neurotol 2006; 11 (suppl 1):27-33, DOI: 10.1159/000095611, Published online Oct. 6, 2006, 7 pages.

(Continued)

*Primary Examiner* — George Manuel
(74) *Attorney, Agent, or Firm* — Edell, Shapiro & Finnan, LLC

(57) ABSTRACT

Presented herein are intra-operative techniques for setting the angular insertion depth of a stimulating assembly during implantation into a recipient's cochlea. In certain embodiments, the angular insertion depth is monitored in real-time and advancement of the stimulating assembly is terminated when a selected angular insertion depth is achieved. In further embodiments, a linear insertion depth that corresponds to a selected angular insertion depth is intra-operatively calculated and advancement of the stimulating assembly is terminated when the calculated linear insertion depth is achieved.

26 Claims, 10 Drawing Sheets

(56) References Cited

U.S. PATENT DOCUMENTS

| | | | |
|---|---|---|---|
| 8,401,665 B2 | 3/2013 | Bradley et al. | |
| 8,532,781 B1 | 9/2013 | Vanpoucke | |
| 8,554,330 B2 | 10/2013 | Bradley et al. | |
| 8,594,799 B2 | 11/2013 | Haller et al. | |
| 2004/0138723 A1 | 7/2004 | Malick et al. | |
| 2007/0179565 A1 | 8/2007 | Overstreet et al. | |
| 2008/0125833 A1 | 5/2008 | Bradley et al. | |
| 2010/0106232 A1 | 4/2010 | Dadd et al. | |
| 2011/0066160 A1 | 3/2011 | Simaan et al. | |
| 2011/0106101 A1 | 5/2011 | Tortonese et al. | |
| 2011/0295352 A1* | 12/2011 | Thenuwara | A61N 1/0541 607/137 |
| 2012/0065705 A1 | 3/2012 | Kals | |
| 2012/0109274 A1 | 5/2012 | Simaan et al. | |
| 2012/0245666 A1 | 9/2012 | Jolly et al. | |
| 2012/0316454 A1 | 12/2012 | Carter | |
| 2013/0138117 A1 | 5/2013 | Abbott et al. | |
| 2013/0331779 A1 | 12/2013 | Dhanasingh et al. | |

OTHER PUBLICATIONS

International Search Report and Written Opinion in counterpart International Application No. PCT/IB2015/056668, mailed Dec. 17, 2015, 11 pages.

\* cited by examiner

INTRA-COCHLEAR STIMULATING ASSEMBLY INSERTION

CROSS-REFERENCE TO RELATED APPLICATIONS

This application claims priority to U.S. Provisional Application No. 62/044,599 entitled "Intra-cochlear Stimulating Assembly Insertion," filed Sep. 2, 2014, the content of which is hereby incorporated by reference herein.

BACKGROUND

Field of the Invention

The present invention relates generally to cochlear implants.

Related Art

Hearing loss, which may be due to many different causes, is generally of two types, conductive and/or sensorineural. Conductive hearing loss occurs when the normal mechanical pathways of the outer and/or middle ear are impeded, for example, by damage to the ossicular chain or ear canal. Sensorineural hearing loss occurs when there is damage to the inner ear, or to the nerve pathways from the inner ear to the brain.

Individuals who suffer from conductive hearing loss typically have some form of residual hearing because the hair cells in the cochlea are undamaged. As such, individuals suffering from conductive hearing loss typically receive an auditory prosthesis that generates motion of the cochlea fluid. Such auditory prostheses include, for example, acoustic hearing aids, bone conduction devices, and direct acoustic stimulators.

In many people who are profoundly deaf, however, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate nerve cells of the recipient's auditory system in other ways (e.g., electrical, optical and the like). Cochlear implants are often proposed when the sensorineural hearing loss is due to the absence or destruction of the cochlea hair cells, which transduce acoustic signals into nerve impulses. Auditory brainstem stimulators might also be proposed when a recipient experiences sensorineural hearing loss due to damage to the auditory nerve.

SUMMARY

In one aspect of the invention, a method is provided. The method comprises: during insertion of an elongate stimulating assembly comprising a plurality of longitudinally spaced contacts into a recipient's cochlea, performing one or more electrical measurements, and based on the one or more electrical measurements, setting an angular position for the distal end of the stimulating assembly.

In another aspect of the invention, a system is provided. The system comprises a cochlear implant comprising an implantable stimulator unit, and an elongate stimulating assembly comprising a plurality of longitudinally spaced contacts configured to be inserted into a recipient's cochlea. The system also comprises a processor configured to: during insertion of the stimulating assembly into the cochlea, perform one or more electrical measurements, and based on the one or more electrical measurements, set an angular insertion depth for the stimulating assembly.

In another aspect of the invention, a method is provided. The method comprises while inserting a stimulating assembly into the cochlea of a recipient, performing a plurality of electrical measurements between two or more contacts, and evaluating the electrical measurements relative to one another to determine a real-time angular position of the stimulating assembly.

In another aspect of the invention, a method is provided. The method comprises while inserting a stimulating assembly into the cochlea of a recipient, measuring a length of a basal region of the cochlea, calculating, based on measured length of the basal region, a size of the cochlea, and based on the calculated size of the cochlea, determine a linear insertion depth of the stimulating assembly that corresponds to a selected angular insertion depth for the stimulating assembly.

BRIEF DESCRIPTION OF THE DRAWINGS

Embodiments of the present invention are described herein in conjunction with the accompanying drawings, in which.

DETAILED DESCRIPTION

Presented herein are intra-operative techniques for setting the angular insertion depth of a stimulating assembly during implantation into a recipient's cochlea. In certain embodiments, the angular insertion depth is monitored in real-time during insertion of the stimulating assembly and advancement of the stimulating assembly is terminated when a selected angular insertion depth is achieved. In further embodiments, a linear insertion depth that corresponds to a selected angular insertion depth is intra-operatively calculated and advancement of the stimulating assembly is terminated when the calculated linear insertion depth is achieved.

Figure 1:
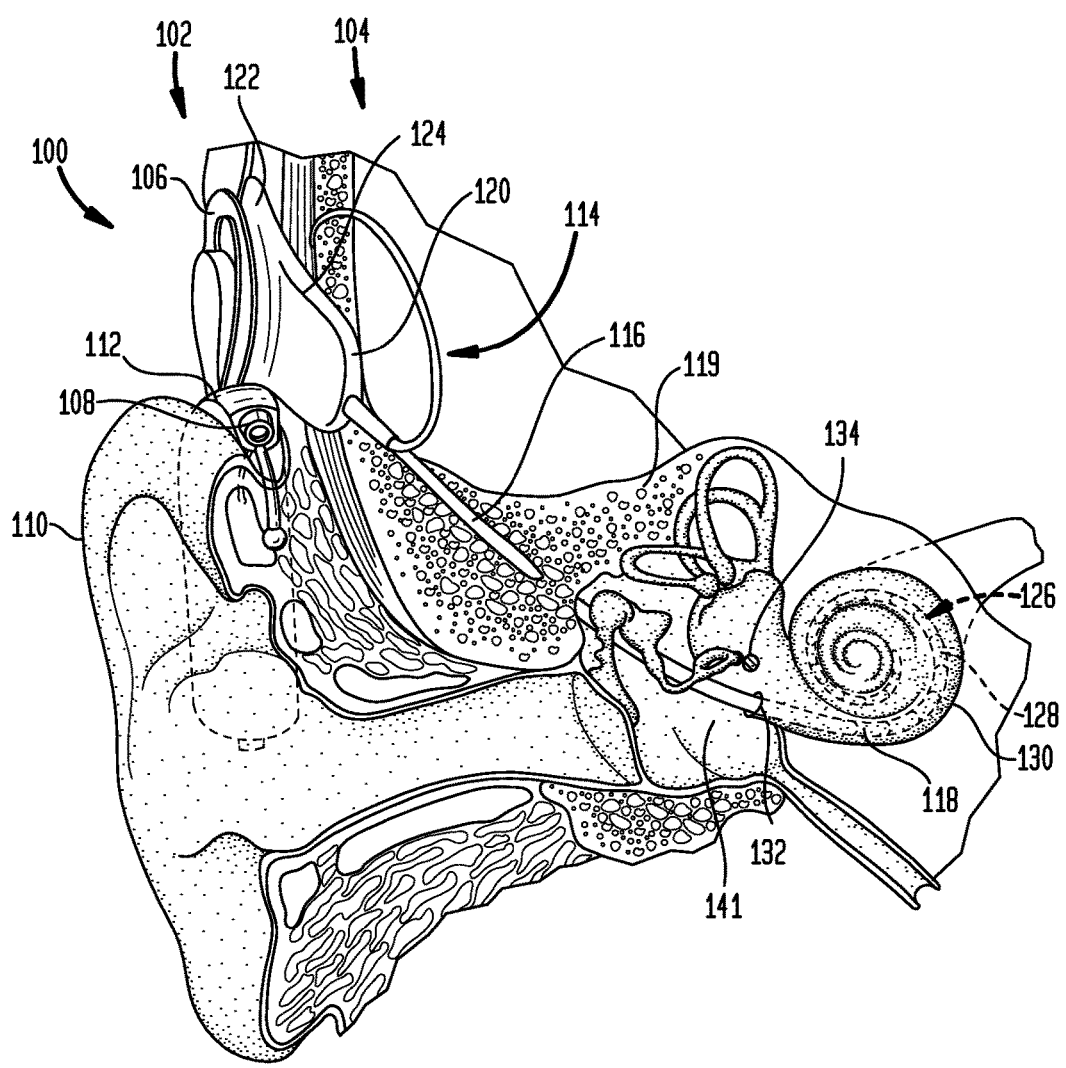
FIG. 1 is a schematic diagram of a cochlear implant configured to implement techniques in accordance with embodiments presented herein.

FIG. 1 is perspective view of an exemplary cochlear implant 100 that may be implanted in a recipient using the angular insertion depth setting techniques in accordance with embodiments presented herein. The cochlear implant 100 includes an external component 102 and an internal/ implantable component 104. The external component 102 is directly or indirectly attached to the body of the recipient and typically comprises an external coil 106 and, generally, a magnet (not shown in FIG. 1) fixed relative to the external coil 106. The external component 102 also comprises one or more sound input elements 108 (e.g., microphones, telecoils, etc.) for detecting sound and a sound processing unit 112. The sound processing unit 112 may include, for example, a power source (not shown in FIG. 1) and a sound processor (also not shown in FIG. 1). The sound processor is configured to process electrical signals generated by a sound input element 108 that is positioned, in the depicted embodiment, by auricle 110 of the recipient. The sound processor provides the processed signals to external coil 106 via a cable (not shown in FIG. 1).

The implantable component 104 comprises an implant body 114, a lead region 116, and an elongate intra-cochlear stimulating assembly 118. The implant body 114 comprises a stimulator unit 120, an internal/implantable coil 122, and an internal receiver/transceiver unit 124, sometimes referred to herein as transceiver unit 124. The transceiver unit 124 is connected to the internal coil 122 and, generally, a magnet (not shown) fixed relative to the internal coil 122.

The magnets in the external component 102 and implantable component 104 facilitate the operational alignment of the external coil 106 with the internal coil 122. The operational alignment of the coils enables the implantable coil 122 to transmit/receive power and data to/from the external coil 106. More specifically, in certain examples, external coil 106 transmits electrical signals (e.g., power and stimulation data) to implantable coil 122 via a radio frequency (RF) link. Implantable coil 122 is typically a wire antenna coil comprised of multiple turns of electrically insulated single-strand or multi-strand platinum or gold wire. The electrical insulation of implantable coil 122 is provided by a flexible molding (e.g., silicone molding). In use, transceiver unit 124 may be positioned in a recess of the temporal bone of the recipient. Various other types of energy transfer, such as infrared (IR), electromagnetic, capacitive and inductive transfer, may be used to transfer the power and/or data from an external device to cochlear implant and FIG. 1 illustrates only one example arrangement.

Elongate stimulating assembly 118 is configured to be at least partially implanted in cochlea 130 and includes a plurality of longitudinally spaced intra-cochlear contacts 128. The contacts 128 collectively form a contact array 126 and may comprise electrical contacts and/or optical contacts.

Stimulating assembly 118 extends through an opening in the cochlea 130 (e.g., cochleostomy 132, the round window 134, etc.) and has a proximal end connected to stimulator unit 120 via lead region 116 that extends through mastoid bone 119. Lead region 116 couples the stimulating assembly 118 to implant body 114 and, more particularly, stimulator unit 120.

An intra-cochlear stimulating assembly, such as stimulating assembly 118, may be a perimodiolar stimulating assembly or a non-perimodiolar stimulating assembly. A perimodiolar stimulating assembly is a stimulating assembly that is configured to adopt a curved configuration during and/or after implantation into the recipient's cochlea so as to have at least the distal section positioned close to the wall of the recipient's modiolus (i.e., close to the modiolar wall). One type of non-perimodiolar stimulating assembly is a lateral stimulating assembly that is configured to be implanted so as to be positioned along the lateral wall of the recipient's scala tympani (i.e., the wall that is opposite the modiolar wall). Another type of non-perimodiolar stimulating assembly is a mid-scala stimulating assembly which assumes a mid-scala position during or following implantation (i.e., positioned approximately midway between the modiolar wall and the lateral wall).

In general, the sound processor in sound processing unit 112 is configured to execute sound processing and coding to convert a detected sound into a coded signal corresponding to electrical signals for delivery to the recipient. The coded signal generated by the sound processor is then sent to the stimulator unit 120 via the RF link between the external coil 106 and the internal coil 122. The stimulator unit 120 includes one or more circuits that use the coded signals, received via the transceiver unit 124, so as to output stimulation (stimulation current) via one or more stimulation channels that terminate in the intra-cochlear stimulating contacts 128. As such, the stimulation is delivered to the recipient via the intra-cochlear stimulating contacts 128. In this way, cochlear implant 100 stimulates the recipient's auditory nerve cells, bypassing absent or defective hair cells that normally transduce acoustic vibrations into neural activity.

Figure 2A:
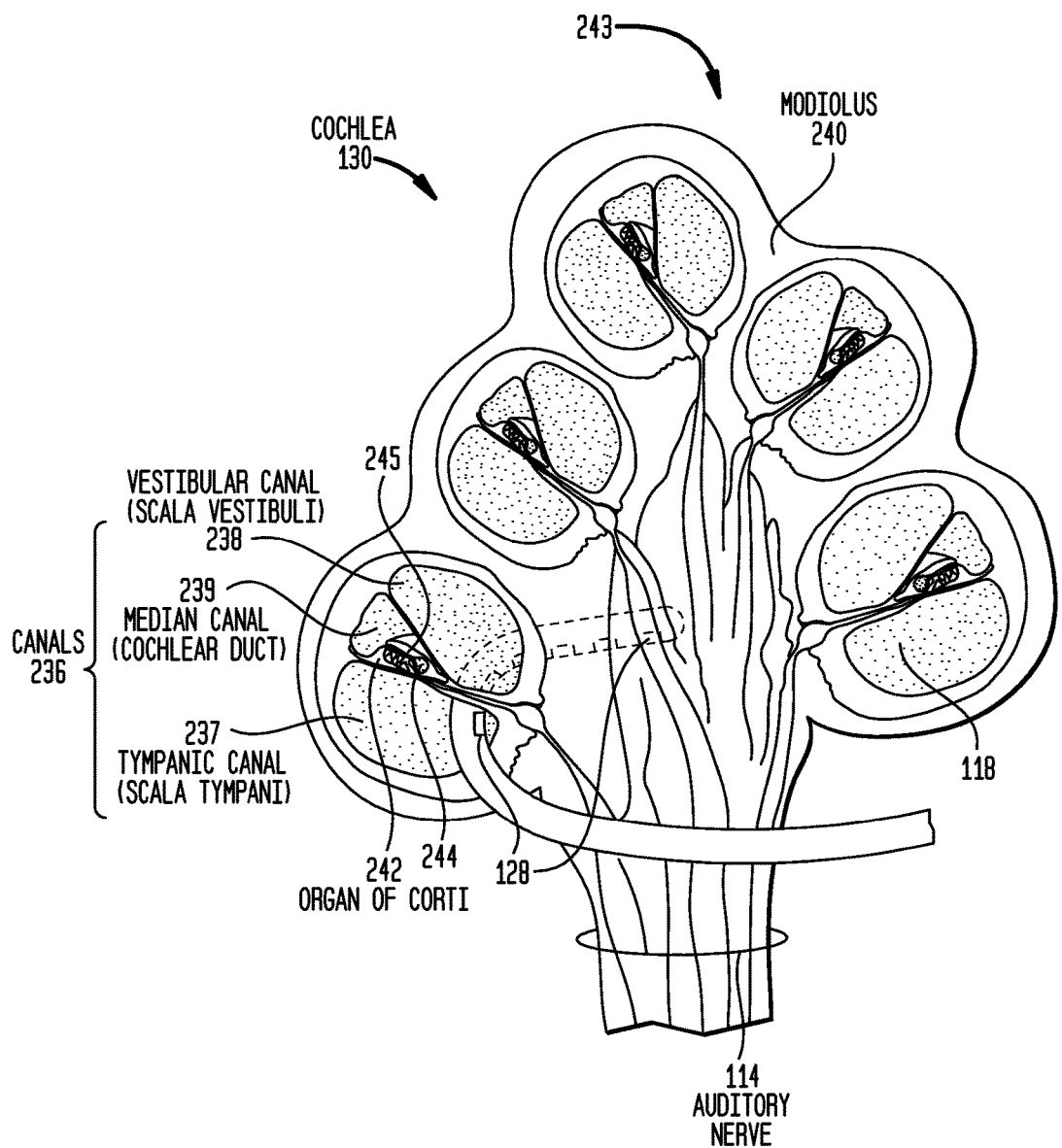
FIG. 2A is a cross-sectional view of a recipient's cochlea that has been partially cut-away to display the canals and to illustrate a position of a stimulating assembly in the cochlea.
Figure 2B:
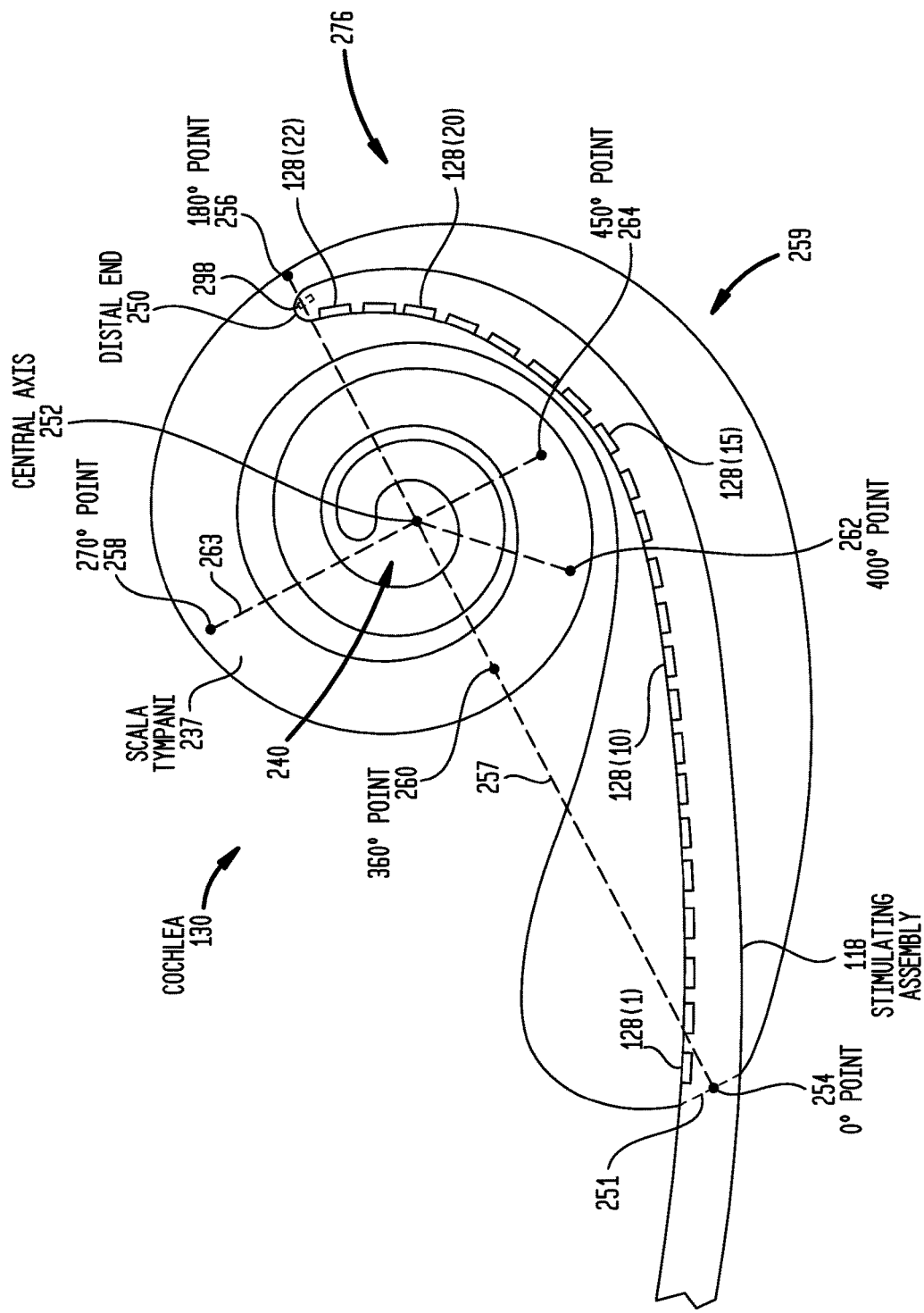
FIG. 2B is a simplified schematic view of the cochlea of FIG. 2A.

FIG. 2A is cross-sectional view of cochlea 130 illustrating stimulating assembly 130 partially implanted therein. FIG. 2B is a simplified top view of cochlea 130 illustrating stimulating assembly 130 partially implanted therein. Referring first to FIG. 2A, cochlea 130 is a conical spiral structure that comprises three parallel fluid-filled canals or ducts, collectively and generally referred to herein as canals 236. Canals 236 comprise the tympanic canal 237, also referred to as the scala tympani 237, the vestibular canal 238, also referred to as the scala vestibuli 238, and the median canal 239, also referred to as the scala media 239. Cochlea 130 includes the modiolus 240 which is a conical shaped central region around which the cochlea canals 236 spiral. The modiolus 240 consists of spongy bone in which the cochlea nerve cells, sometimes referred to herein as the spiral ganglion cells, are situated. The cochlea canals 236 generally turn 2.5 times around the modiolus 240.

To insert intra-cochlear stimulating assembly 118 into cochlea 130, an opening (facial recess) is created through the recipient's mastoid bone 119 (FIG. 1) to access the recipient's middle ear cavity 141 (FIG. 1). The surgeon then creates an opening from the middle ear into the cochlea 130 through, for example, the round window, oval window, the promontory, etc. of the cochlea 130. The surgeon then gently advances (pushes) the stimulating assembly 118 forward into the cochlea 130 until the stimulating assembly 118 achieves a final implanted position. As shown in FIGS. 2A and 2B, the stimulating assembly 118 follows the helical shape of the cochlea 130. That is, the stimulating assembly 118 spirals around the modiolus 212.

In normal hearing, sound entering auricle 110 (FIG. 1) causes pressure changes in cochlea 130 that travel through the fluid-filled tympanic and vestibular canals 237, 238. The organ of Corti 210, which is situated on basilar membrane 244 in scala media 239, contains rows of hair cells (not shown) which protrude from its surface. Located above the hair cells is the tectoral membrane 245 which moves in response to pressure variations in the fluid-filled tympanic and vestibular canals 237, 238. Small relative movements of the layers of membrane 245 are sufficient to cause the hair cells to move, thereby causing the creation of a voltage pulse or action potential which travels along the associated nerve fibers that connect the hair cells with the auditory nerve 246. Auditory nerve 246 relays the impulses to the auditory areas of the brain (not shown) for processing.

Typically, in cochlear implant recipients some portion of the cochlea 130 (e.g., the hair cells) is damaged such that the cochlea cannot transduce pressure changes into nerve impulses for relay to the brain. As such, the contacts 128 of the stimulating assembly 118 are used to directly stimulate the cells to create nerve impulses resulting in perception of a received sound. In the specific embodiments illustrated herein, stimulating assembly 118 comprises twenty-two (22) intra-cochlear contacts 128(1) through 128(22) that may deliver stimulation to the cochlea 130. Contact 128(1) is the most proximal/basal contact (i.e., the contact configured to be implanted closest to the basal end of the cochlea 130), while intra-cochlear contact 128(22) is the most distal/apical contact (i.e., located closed to the cochlea apex 243). Due to the illustrative view, only a subset of the twenty-two (22) intra-cochlear contacts 128(1) through 128(22) are visible in FIG. 2A.

A reference contact (not shown in FIGS. 2A and 2B) may also be provided. The reference contact is positioned outside of the recipient's cochlea 130 and, as such, is sometimes referred to as an extra-cochlear electrode (ECE).

As noted above, the contacts 128(1)-128(22) deliver stimulation to the cochlea 130 to evoke a hearing percept. The effectiveness of the stimulation depends, at least in part, on the place along basilar membrane 244 where the stimulation is delivered. That is, the cochlea 130 has characteristically been referred to as being "tonotopically mapped" in that regions of the cochlea toward the basal end are more responsive to high frequency signals, while regions of cochlea 130 toward the apical end are more responsive to low frequency signals. These tonotopical properties of cochlea 130 are exploited in a cochlear implant by delivering stimulation within a predetermined frequency range to a region of the cochlea that is most sensitive to that particular frequency range. However, this stimulation relies on the particular contacts 128(1)-128(22) having a final implanted positioned adjacent to a corresponding tonotopic region of the cochlea 130 (i.e., a region of the cochlea that is sensitive to the frequency of sound represented by the contact).

To achieve a correct final implanted position, the distal end/tip 250 of the stimulating assembly 118 should be placed at a correct angular position, sometimes referred to herein as a correct angular insertion depth. As used herein, the angular position or angular insertion depth of the stimulating assembly 118 refers to the angular rotation of the distal end 250 from the cochlea opening 251 (e.g., round window, cochleostomy, etc.) through which the stimulating assembly enters the cochlea. As such, the angular position/angular insertion depth may be expressed in terms of how many angular degrees)(° the distal end 250 has traveled within the cochlea 130 with respect to the cochlea opening 251. For example, an angular insertion depth of one hundred and eighty (180) degrees indicates that the distal end 250 has traveled around half (½) of the first turn 276 of cochlea 130. An angular insertion depth of three hundred and sixty (360) degrees indicates that the distal end 250 has traveled completely around the first turn 276. Angular insertion depth, if achieved accurately, is a constant for all recipients that enables correct frequency alignment (i.e., positioning of the contacts 128(1)-128(22) adjacent to a corresponding tonotopic region of the cochlea 130.

However, a problem arises due to the fact the size of the cochlea may vary from recipient to recipient. These different cochlea sizes result in cochlea turns that have different radii, thereby resulting in different linear lengths to achieve an angular insertion depth. For example, an angular insertion of 360 degrees for one recipient may require a linear insertion depth of 6 millimeters (mm), while the same angular insertion depth of 360 degrees may require a linear insertion depth of 8 mm for a different recipient. The linear insertion depth of a stimulating assembly refers to the linear length of the stimulating assembly that is within the cochlea (i.e., has passed through the cochlea opening).

The cochlea 130 shown in FIG. 2B is defined so as to include a central axis 252 extending generally through the geometric center of the cochlea (e.g., through modiolus 240). The cochlea 130 is further defined to include a plurality of different angular reference points with respect to the central axis 252. In particular, a zero (0) degree angular reference point (0° point) 254 is a point within the scala tympani 237 that is located at or adjacent to the cochlea opening 251 through which the stimulating assembly 118 is inserted. A one hundred and eighty (180) degree angular reference point (180° point) 256 is a point within the scala tympani 237 that is diametrically opposite from the 0° point 254 (i.e., 180° point 256 is located on the opposite side of the modiolus 240 from 0° point 254). The 0° point 254 and 180° point 256 both lie within a reference plane 257 that passes through the central axis 252. As noted above, the scala tympani 237 spirals around the modiolus 240. As such, the 180° point 256 is further "up" the cochlea spiral (i.e., at a different level within the reference plane 257) than the 0° point 254.

FIG. 2B illustrates the distal end 250 of the stimulating assembly 118 positioned at the 180° point 256. The distal end 250 of the stimulating assembly 118 reaches the 180° point 256 after the surgeon pushes the stimulating assembly 118 through the scala tympani 237 past the beginning 259 of the basal (first) turn 276.

In FIG. 2B, the cochlea 130 also includes a two hundred and seventy (270) degree angular reference point (270° point) 258, a three hundred and sixty (360) degree angular reference point (360° point) 260, a four hundred (400) degree angular reference point (400° point) 262, and a four hundred and fifty (450) degree angular reference point (450° point) 264. The 360° point 260 is located diametrically opposite the 180° point 256 and lies within reference plane 257. More specifically, the 360° point 260 is located between the 0° point 254 and the 180° point 256. However, since as noted above the scala tympani 237 spirals around the modiolus 240, the 360° point 260 is further up the cochlea spiral (i.e., at a different level within the reference plane 257) than both the 0° point 254 and the 180° point 256.

The 270° point 258 is a point within scala tympani 237 located at an angular position midway between the 180° point 256 and the 360° point 260. The 450° point 264 is a point within the scala tympani 237 that is diametrically opposite from the 270° point 258 (i.e., 450° point 264 is located on the opposite side of the modiolus 240 from 270° point 258). The 270° point 258 and the 450° point 264 both lie within a reference plane 263 that passes through the central axis 252. Since the scala tympani 237 spirals around the modiolus 240, the 450° point 264 is further up the cochlea spiral (i.e., at a different level within the reference plane 263) than both the 270° point 258. The 400° point 262 is a point within the scala tympani 237 that is located between the 360° point 260 and the 450° point 264 (i.e., a point 40 degrees after the 360° point 260 and 50 degrees before the 450° point 264).

In FIG. 2B, specific angular reference points have been selected and shown merely for ease of description. It is to be appreciated that a number of other angular reference points may be defined and used in accordance with embodiments presented herein.

In conventional intra-cochlear stimulating assembly insertion techniques, the surgeon operates "blind." That is, due to the nature of the access (through the facial recess and the middle ear cavity), the surgeon cannot actually see the stimulating assembly 118 once it passes into the cochlea 130. Therefore, the surgeon is unaware of the actual location of the distal end 250 of the stimulating assembly 118. Instead, a surgeon typically inserts the stimulating assembly until met with resistance (i.e., relies upon only touch/feel during the insertion). Certain conventional techniques may be based on the "average" cochlea size and do not account for recipient-specific variations in cochlea size. Other conventional techniques require pre-operative imaging of the cochlea. A technician or other user manually estimates the size of the recipient's cochlea based on the pre-operative image and the size estimate is used in an attempt to achieve the correct angular insertion depth of the distal end 250. Conventional techniques that rely upon estimations of the cochlea size may result in incorrect positioning of the stimulating assembly 118 and thus misalignment of the contacts 128 with the corresponding frequency regions of the cochlea 130.

As such, presented herein are techniques for intra-operative setting the angular insertion depth of a cochlear implant stimulating assembly. For ease of illustration, the intra-operative angular insertion depth determination techniques are primarily described herein with reference to implantation of stimulating assembly 118 into cochlea 130 as described with reference to FIGS. 1, 2A, and 2B.

Figure 3:
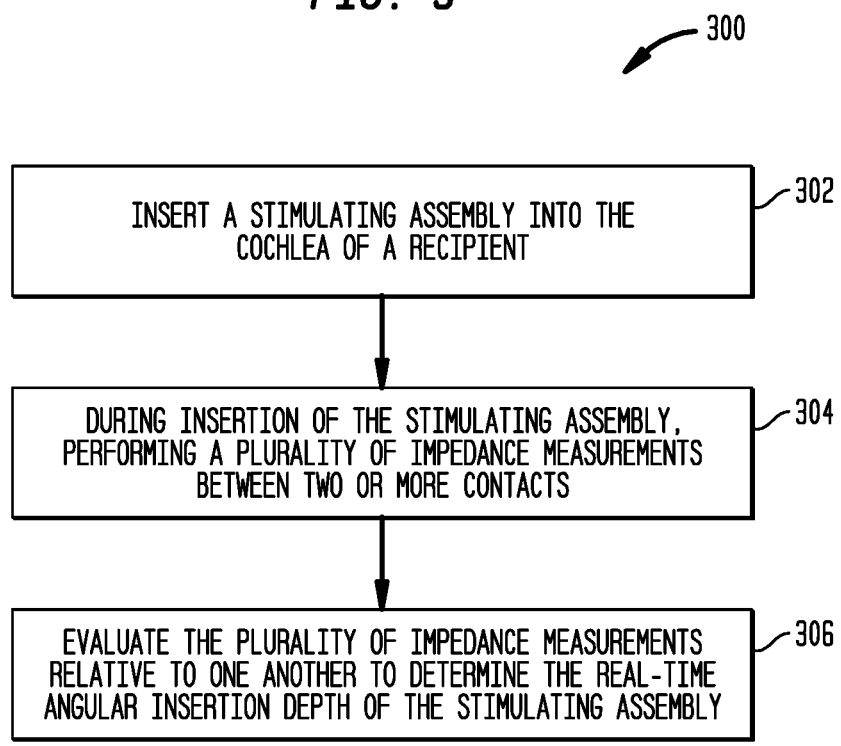
FIG. 3 is a flowchart of an intra-operative method in accordance with embodiments presented herein.

FIG. 3 is a flowchart of a first intra-operative method 300 for setting the angular insertion depth of stimulating assembly 118. FIG. 3 illustrates a real-time method that enables the determination of the current/present (i.e., actual) angular insertion depth of stimulation assembly 118 within cochlea 130.

Method 300 begins at 302 where stimulating assembly 118 is at least partially inserted into cochlea 130. At 304, during insertion of the stimulating assembly into the cochlea, the impedance between different pairs of intra-cochlear contacts of the stimulating assembly 118 is measured and used to determine the angular insertion depth of the stimulating assembly.

In one embodiment, to measure the impedance between two intra-cochlear contacts, bipolar electrical stimulation (i.e., one or more bipolar current signals) is repeatedly delivered between a first intra-cochlear contact and a second intra-cochlear contact. After the delivery of each set of bipolar stimulation between the first and second intra-cochlear contacts, the impedance between the first and second contacts is measured (e.g., at the second intra-cochlear contact). The contact that delivers the current signals is sometimes referred to herein as the "stimulating" or "source" contact and the contact that sinks the current is sometimes referred to herein as the "return" contact. Additionally, the two contacts between which the stimulation is delivered are sometimes collectively referred to herein as a "stimulating pair." The remaining contacts that are not part of the stimulating pair are disconnected from the system ground (i.e., are electrically "floating").

It is to be appreciated that impedance measurements are made between two points, thus the impedance may be "measured" at either of the two points (i.e., it is a relative measurement between those two points). However, merely for ease of illustration of certain embodiments presented herein, the return contact of the stimulating pair is sometimes referred to herein as a "measurement" contact.

In general, the impedance between two intra-cochlear contacts in a stimulating pair can be correlated to their physical proximity with one another and their location in the cochlea. The physically closer the contacts of the stimulating pair are to one another, the lower the impedance that will be measured between the contacts. At 306, again while inserting the stimulating assembly 118, the impedance-to-proximity relationship is used to evaluate the plurality of impedance measurements relative to one another to determine the relative proximity between the two or more intra-cochlear contacts and thus determine the real-time (current/present) angular insertion depth of the stimulating assembly 118. As described further below, the method includes the selection one or more sets/pairs of intra-cochlear contacts for impedance measurement that have a relationship to one another that enables the angular insertion depth of the stimulating assembly 118 to be determined from the relative proximity of the one or more pairs of intra-cochlear contacts.

In certain embodiments of FIG. 3, the two or more intra-cochlear contacts selected for impedance measurement comprise two specific (static contacts) that have a maximum physical separation when the angular insertion depth of the stimulating assembly 118 is 180° (i.e., the distal end 250 of the stimulating assembly 118 is inserted to 180° point 256), and a minimum physical separation when the angular insertion depth of the stimulating assembly 118 is 360° (i.e., the distal end 250 of the stimulating assembly 118 is inserted to 360° point 260). This relationship between contacts having a maximum and minimum separation arrangement at the specific 180° and 360° points is referred to herein as an angular proximity relationship.

Depending on, for example, the shape, size, length, etc. of a stimulating assembly, different contacts may have an angular proximity relationship. As such, different stimulating pairs of contacts may be used in accordance in different embodiments to determine the angular insertion depth of the stimulating assembly 118. Therefore, in certain embodiments, the method includes determining and selecting the one or more pairs of intra-cochlea contacts that are believed to have a correct angular proximity relationship.

Figure 4:
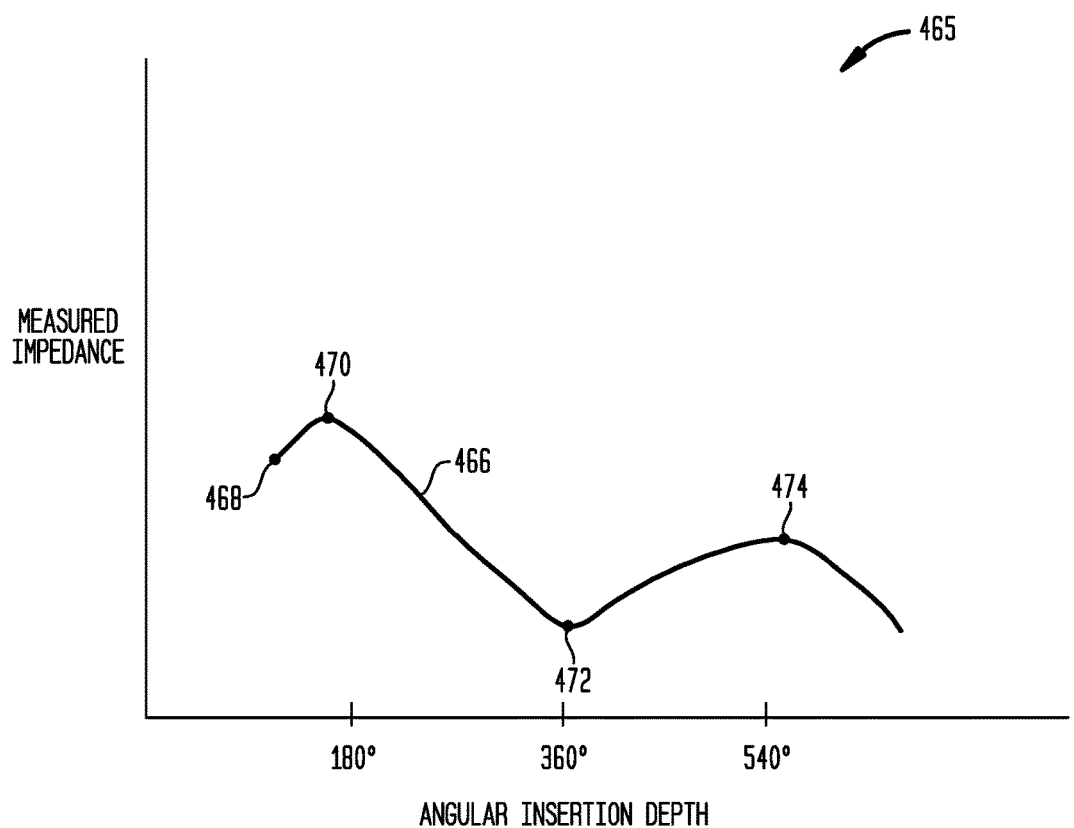
FIG. 4 is a plot of example impedance measurements obtained during a method in accordance with embodiments presented herein.

For example, in one illustrative embodiment, the most distal/apical contact 128(22) and the most proximal/basal contact 128(1) have an angular proximity relationship that enables the use of impedance measurements between these two contacts to determine the angular insertion of the stimulating assembly 118. More specifically, FIG. 4 is a graph 465 that illustrates impedances measured between contacts 128(22) and 128(1) over a period of time during insertion of stimulating assembly 118. The graph 465 has a vertical (Y) axis that represents the measured impedance and a horizontal (X) axis that represents the angular insertion depth of the stimulating assembly.

In the embodiment of FIG. 4, bipolar stimulation is delivered between contact 128(22) and contact 128(1) and the impedance between the contacts is measured. This process is repeated over a period of time to produce a plurality of impedance measurements. These impedance measurements are plotted as an impedance curve 466. As shown, the measurement of the impedance between contacts 128(22) and 128(1) begins at point 468 of the impedance curve 466. The measurement of the impedance between contacts 128(22) and 128(1) may begin, for example, when contact 128(1) enters the cochlea through opening 251 and may continue while the stimulating assembly 118 is inserted into the cochlea 130. In general, the contacts 128(1)-128(22) experience a significant impedance change after entering into the cochlea 130 (e.g., due to immersion in the conductive perilymph). As such, the system can monitor the impedance at the contact 128(1) to determine when the contact enters the cochlea 130.

As noted above, FIG. 4 illustrates the measured impedance plotted against the angular insertion depth of the stimulating assembly 118. The impedance rises from starting point 468 to a first peak/maximum at point 470. The impedance subsequently falls to a minimum at point 472, then again rises to second peak/maximum at point 474. Because the impedance between contacts 128(22) and 128(1) is a maximum at point 470, point 470 indicates that the stimulating assembly 118 has been inserted 180 degrees (i.e., the contacts 128(22) and 128(1) are at the maximum possible distance from one another within cochlea 130). Stated differently, this first maximum point 470 indicates that the distal end 250 of stimulating assembly 118 has reached 180° point 256 (FIG. 2B), while contact 128(1) is relatively close to 0° point 254 (FIG. 2B)

Similarly, because the impedance between contacts 128(22) and 128(1) is a minimum at point 472, point 472 indicates that the stimulating assembly 118 has been inserted 360 degrees (i.e., the contacts 128(22) and 128(1) are at the minimum possible distance from one another within cochlea 130). Stated differently, this minimum point 472 indicates that the distal end 250 of stimulating assembly 118 has reached 360° point 260 (FIG. 2B), while contact 128(1) is located within the basal region of cochlea 130 substantially close to 360° point 260 (i.e., the contacts 128(22) and 128(1) are physically close together, but separated by a section of the modiolus 240).

The second maximum 474 indicates a location of distal end 250 of stimulating assembly 118 at which the impedance between contacts 128(22) and 128(1) is a second maximum. That is, the stimulating assembly 118 has been inserted another 180 degrees from the minimum point 472 such that the stimulating assembly 118 is at an angular insertion depth of 540 degrees.

Figure 5:
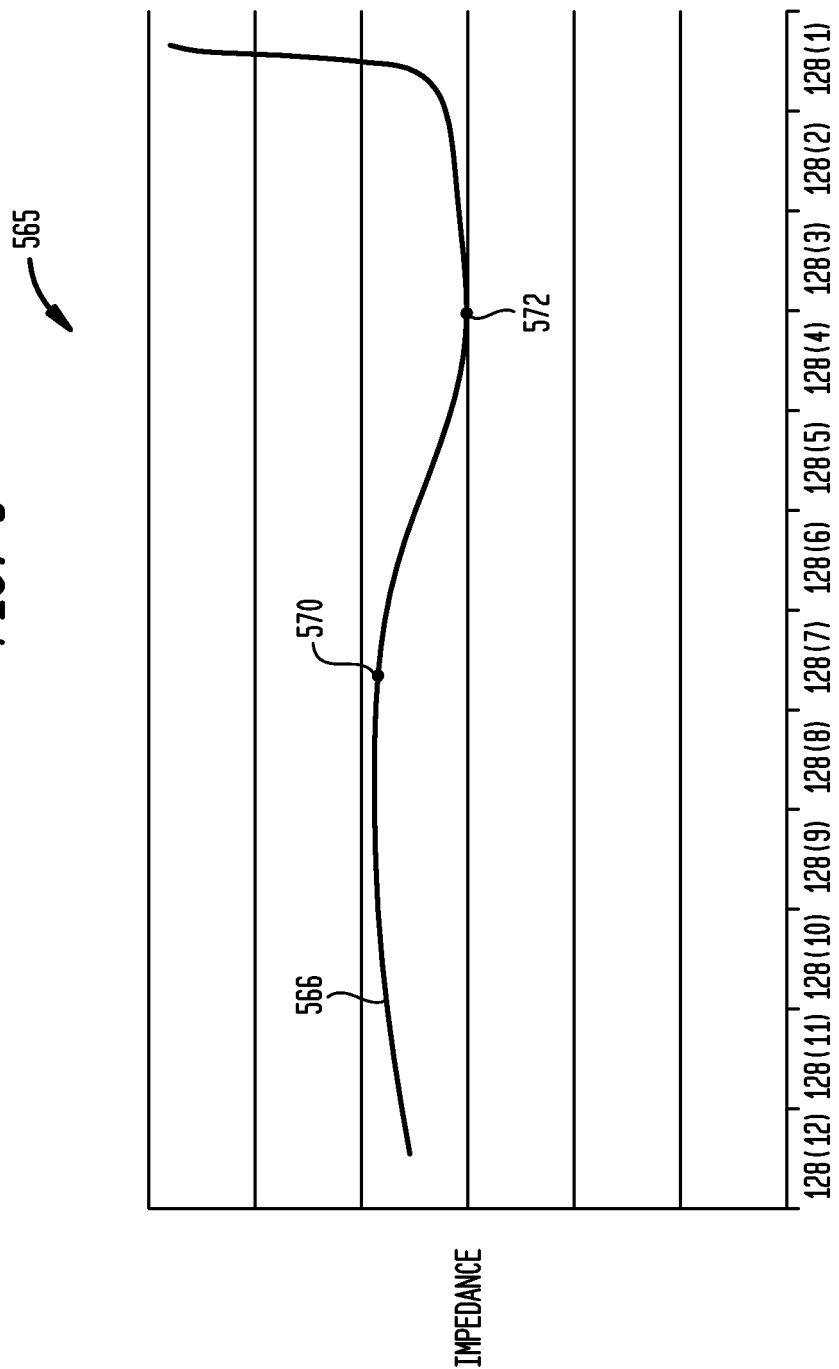
FIG. 5 is a plot of example impedance measurements obtained during a method in accordance with embodiments presented herein.

In summary, FIG. 4 illustrates an embodiment of FIG. 3 in which the impedance between two selected contacts is monitored and evaluated to determine the angular insertion depth of the stimulating assembly 118. In further embodiments of FIG. 3, the impedances between different pairs of contacts may be monitored and simultaneously evaluated to determine the angular insertion depth of stimulating assembly 118. For example, FIG. 5 is a graph 565 illustrating a curve 566 of the impedance measured between contact 128(22) and each of the contacts 128(12) through 128(1) during insertion of stimulating assembly 118. The graph 565 has a vertical (Y) axis that represents the measured impedance and a horizontal (X) axis that represents contacts 128(12) through 128(1).

In contrast to graph 465 that illustrates the measured impedance values between two specific contacts over a period of time, graph 565 illustrates the impedance values measured between 128(22) and each of a plurality of contacts 128(12) through 128(1) at a particular instant while the stimulating assembly 118 is at a specific location. The impedance curve 566 may be generated by sequentially delivering bipolar stimulation between stimulating contact 128(22) and each of the return contacts 128(12)-128(1), and measuring the impedance at each contact (i.e., sequentially changing the return contact for the bipolar stimulation measuring the impedance between the present return contact and the stimulating contact).

In the example of FIG. 5, contact 128(1) is located near the cochlea opening 251. Maximum impedance, shown by point 570, is measured at contact 128(7). This maximum at contact 128(7) indicates that the impedance measured between stimulating contact 128(22) and 128(7) is greater than the impedance measured between stimulating contact 128(22) and each of the other return contacts 128(12)-128(8) and 128(6)-128(1). Therefore, at the instant location of stimulating assembly 118, contact 128(7) is farthest away from stimulating contact 128(22). Additionally, minimum impedance, shown by point 572, is measured at contact 128(4). This minimum at contact 128(4) indicates that the impedance measured between stimulating contact 128(22) and 128(4) is less than the impedance measured between stimulating contact 128(22) and each of the other return contacts 128(12)-128(5) and 128(3)-128(1). Therefore, at the instant location of stimulating assembly 118, contact 128(4) is closest to stimulating contact 128(22).

The measured impedance values and the corresponding relative proximities between the stimulating contact 128(22) and the various return contacts can be utilized to determine the current angular insertion depth of the stimulating assembly 118. For example, the locations of the maximum and minimum shown in FIG. 5 indicate that the stimulating assembly 118 has an angular insertion depth of approximately 400 degrees (i.e., distal end 250 has reached 400° point 262).

In accordance with embodiments of FIGS. 3, 4, and 5, feedback may be generated that indicates to a surgeon or other user the real-time angular insertion depth of a stimulating assembly. For example, in one illustrative embodiment, plots or graphs, such as those shown in FIGS. 4 and 5, may be generated and displayed to a surgeon. The surgeon could use the plots to determine the current angular insertion depth of the stimulating assembly. It is to be appreciated that the plots shown in FIGS. 4 and 5 are merely illustrative and that other plots may be used in further embodiments.

In another embodiment, feedback in the form of a numerical/text display of the determined angular insertion depth may be provided to the surgeon. In further embodiments, audible, tactile, etc. feedback could be provided to a surgeon to indicate the real-time angular insertion depth of the stimulating assembly. For example, an audible beep or tone could be generated as the stimulating assembly reaches predetermined reference points (e.g., angular insertion depths of 180, 270, 360, 400, and 450 degrees). The tones may change to indicate the current angular insertion depth (e.g., one beep at the first reference point, two beeps at the second reference point, and so on).

In a still further embodiment, a two-dimensional (2-D) or three-dimensional (3-D) image of a cochlea may be displayed at a display screen. A corresponding 2-D or 3-D image of a stimulating assembly may also be displayed at the display screen. As a stimulating assembly is inserted into a recipient's cochlea, the location of the stimulating assembly shown on display screen may be corresponding updated so that the surgeon can visualize the real-time location of the stimulating assembly in the cochlea.

The embodiments of FIGS. 3, 4, and 5 have also been described with reference to measurement of impedance between two or more intra-cochlear contacts of only a single (i.e., one) implanted stimulating assembly and the relative evaluation of the measured impedances to determine the angular insertion depth of that stimulating assembly. It is to be appreciated that embodiments presented herein may use other relative electrical measurements (e.g., voltage) in a similar manner as described above to determine the real-time angular insertion depth of a stimulating assembly.

In summary, FIGS. 3, 4, and 5 illustrate techniques for determining the real-time angular insertion depth of the stimulating assembly. These techniques generate feedback to a surgeon that enables the surgeon to precisely place the stimulating assembly at a selected implanted position. The techniques may facilitate improved hearing performance and increase the preservation of residual hearing. These techniques also eliminate the need for pre or post-operative imaging and the need to use stimulating assemblies having different lengths for different recipients.

As noted above, cochlea size can vary for different recipients. As such, presented herein are further intra-operative techniques that enable a surgeon or other user to measure the size of a recipient's cochlea and use this size measurement to determine a linear insertion depth for a stimulating assembly that is needed to achieve a selected angular insertion depth. As noted above, the angular insertion depth of a stimulating assembly refers to the angular rotation of the distal end of the stimulating assembly from the cochlea opening. During implantation of a stimulating assembly, the stimulating assembly is initially held straight so that it can be inserted into the straight basal region of the cochlea. The stimulating assembly then "bends" or "turns" as it passes through the cochlea turns. As noted above, the linear insertion depth of a stimulating assembly refers to the linear length of the stimulating assembly that is within the cochlea (i.e., has passed through the cochlea opening).

Figure 6:
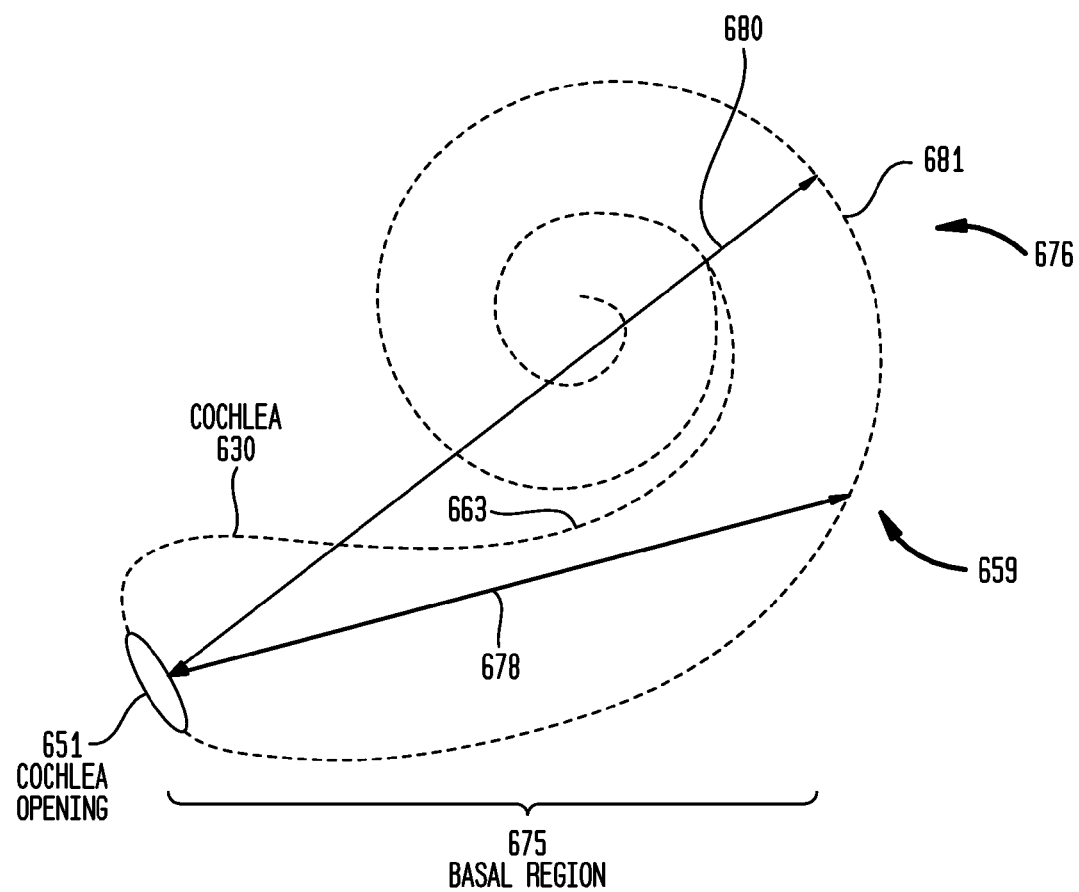
FIG. 6 is a simplified schematic view of a recipient's cochlea.

FIG. 6 is a simplified schematic diagram illustrating dimensions of a cochlea 630 that may be intra-operatively measured for determination of the size of the cochlea. Cochlea 630 includes a cochlea opening 651 (e.g., round window, cochleostomy, etc.) and a basal region 675. The basal region 675 extends from the cochlea opening 651 to the beginning 659 of the first (basal) turn 676 of the cochlea 630. In other words, the basal region 675 is the straight region of the cochlea 630 that is proximal to the first turn 676 of the cochlea. The beginning 659 of the first turn 676 of the cochlea is also the distal end of the basal region 675 (i.e., reference 659 refers to both the beginning of the first turn 676 and the end of the basal region 675).

In FIG. 6, the length of the basal region 675 is represented by bi-directional arrow 678. Additionally, the largest distance from the cochlea opening 651 to the lateral (outside) wall 681 of the cochlea 630 is represented by bi-directional arrow 680.

Figure 7:
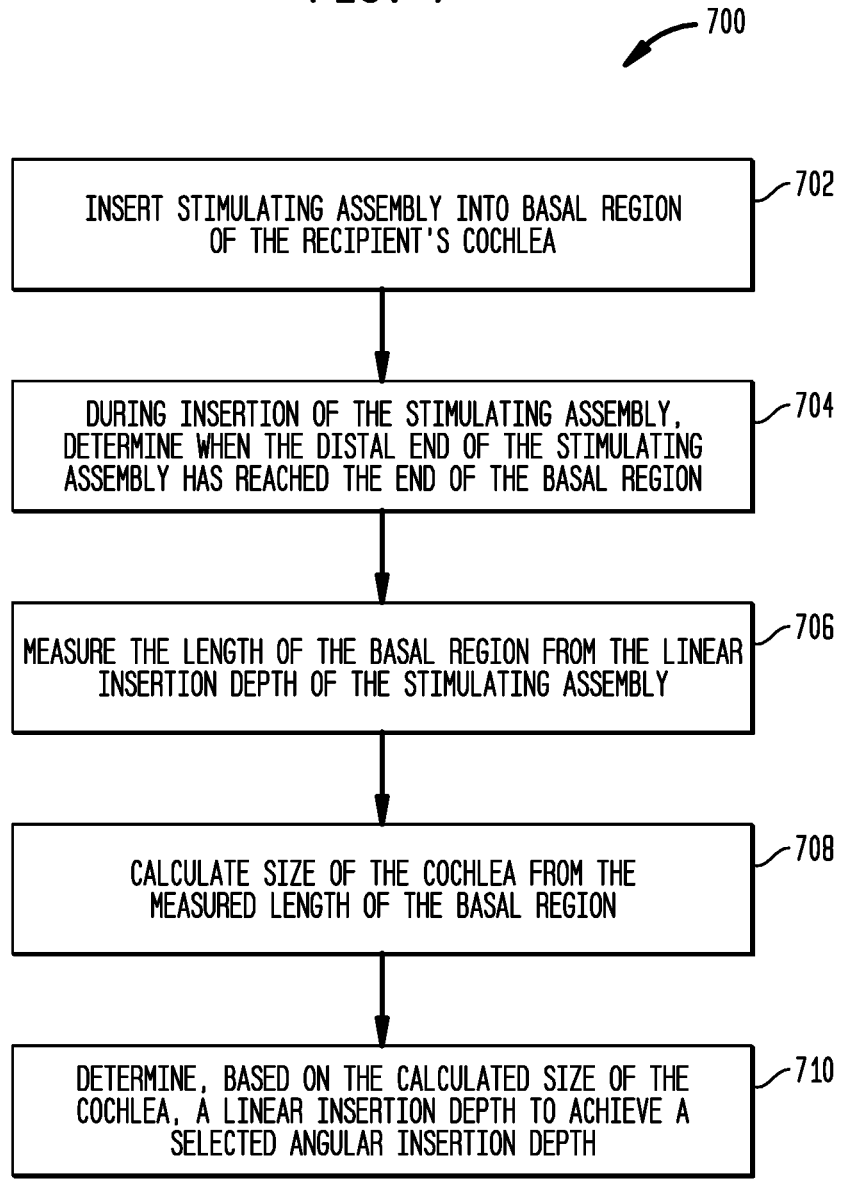
FIG. 7 is a flowchart of another intra-operative method in accordance with embodiments presented herein.

FIG. 7 is a flowchart of a method 700 for the intra-operative determination of the size of a recipient's cochlea. For ease of illustration, the method 700 is described with reference to insertion of stimulating assembly 118 (described above) into cochlea 630 shown in FIG. 6.

Method 700 begins at 702 where the stimulating assembly 118 is partially inserted into cochlea 630. At 704, a determination is made that the distal end 250 of the stimulating assembly 118 is positioned at the distal end 659 of the basal region 675 (i.e., that the distal end 250 has reached the beginning of the first turn 676 of the cochlea 630). In one embodiment, the most distal contact 128(22) is configured to detect an impedance change that indicates the distal end 250 is adjacent to, or is in contact with, the wall of the cochlea 630 located at the distal end 659 of the basal region 675.

In an alternative embodiment, a sensor 298 (shown in FIG. 2B) is positioned at the distal end 250 of the stimulating assembly 118 and is configured to determine when the distal end 250 is adjacent to, or is in contact with, the wall of the cochlea 630 located at the distal end 659 of the basal region 675. In one specific embodiment, the sensor 298 is an impedance sensor (e.g., conductive contact) configured to detect an impedance change that indicates the distal end 250 is adjacent to, or is in contact with, the wall of the cochlea 630 located at the distal end 659 of the basal region 675. In another embodiment, the sensor 298 is a pressure sensor configured to detect when the distal end 250 contacts the wall of the cochlea 630 located at the distal end 659 of the basal region 675. It is to be appreciated that the use of a separate sensor is merely illustrative. It is also to be appreciated that reference to the use of an impedance or pressure sensor is also illustrative and that other sensors may be used in alternative embodiments to detect when the distal end 250 of the stimulating assembly 130 reaches the distal end 659 of the basal region 675.

When it is determined that the distal end 250 of the stimulating assembly 118 is positioned at the distal end of the basal region 675, the length of the basal region 675 is measured. The length of the basal region 675 is measured to be the current/present linear insertion depth of the stimulating assembly 118. As noted above, the stimulating assembly 118 is implanted in a substantially straight configuration and remains substantially straight until reaching the first turn 676 of the cochlea 630. As such, the linear insertion depth of the stimulating assembly 118 (i.e., how far the stimulating assembly is inserted past the cochlea opening 651) when the distal end 250 of the stimulating assembly 118 is positioned at the distal end of the basal region 675 corresponds to the length of the basal region.

In one embodiment, the linear insertion depth of the stimulating assembly 118 is calculated by determining the last contact 128 to enter the cochlea 630 through cochlea opening 651. As noted above, the contacts 128 experience a significant impedance change after entering into the cochlea (e.g., due to immersion in the conductive perilymph). As such, the system can monitor the impedance at the contacts 128 and determine which contacts are inside the cochlea 630 and which contacts are outside of the cochlea. With pre-determined knowledge of the physical configuration of the stimulating assembly 118 (e.g., contact spacing, distance measurements between different portions of the stimulating assembly, etc.), the distance between the distal end 250 and the last contact to enter the cochlea 630 can be calculated as the linear insertion depth and thus the length of the basal region 675.

It is to be appreciated that the above described method for calculating the insertion depth is illustrative and that other methods are possible. For example, in certain arrangements the stimulating assembly 118 includes markings (e.g., visual, tactile, etc.) that indicate a distance from the marking to the distal end 250. In certain embodiments, these markings can be used to calculate the linear insertion depth of the stimulating assembly 118 when the distal end 250 of the stimulating assembly 118 is positioned at the distal end 659 of the basal region 675.

The length of the basal region is referred to herein as being intra-operative measured as it is based on intra-operative operations. These operations produce an accurate measurement that is specific to the recipient's particular cochlea.

Returning to the example of FIG. 7, at 708 the size of the cochlea is calculated from the measured length 678 of the basal region 675. In particular, it has been shown that the length 678 of a recipient's basal region 675 is largely correlated to the largest distance 680 from the cochlea opening 651 to the lateral wall 681 of the cochlea 630. In turn, the largest distance 680 from the cochlea opening 651 to the lateral wall 681 of the cochlea 630 can be used to calculate the size of the cochlea 630.

As used herein, the calculation of the size of cochlea 630 may refer to a determination of all or one or more specific dimensions of the cochlea 630. In one specific example, the determination of the size of the cochlea 630 refers to a determination of the linear length of the lateral wall 681 and/or the linear length of the modiolar wall 683 (FIG. 6) to reach a selected angular insertion depth. For example, the linear/path length (L) of the lateral wall 681 of the cochlea 630 to reach a selected angular insertion depth (θ) may be given as shown below in Equation 1:

$$L = 2.62A \times \log e(1.0 + \theta/235), \quad \text{Equation 1:}$$

where A is the largest distance 680 from the cochlea opening 651 to the lateral wall 681 of the cochlea 630.

Assuming a lateral insertion (i.e., an insertion where the stimulating assembly 118 follows the lateral wall 681 of the cochlea 630), the linear insertion depth of stimulating assembly 118 to reach the selected angular insertion depth (θ) is equal to the path length (L) calculated in Equation 1, above. In a perimodiolar insertion (i.e., an insertion where the stimulating assembly 118 generally follows the modiolar wall 683) or a mid-scala insertion (i.e., an where the stimulating assembly 118 is approximately midway between the lateral and modiolar walls), predetermined offsets from the path length (L) calculated in Equation 1 may be used to calculate the proper perimodiolar or mid-scala insertion depths. In alternative embodiments, additional equations may be utilized to directly calculate the perimodiolar or mid-scala insertion depths.

Feedback may be generated to the surgeon or other user that indicates the linear insertion depth of stimulating assembly 118 needed to reach a selected angular insertion depth. For example, feedback in the form of a numerical/text display of the determined linear insertion depth may be provided to the surgeon. In accordance with certain embodiments, the stimulating assembly 118 may include visual or tactile markers indicating different linear insertion depths (e.g., one marker every 2 mms). A surgeon could use these markers to insert the stimulating assembly 118 to the selected linear depth.

In certain embodiments, after measurement of the size of the recipient's cochlea, a surgeon may enter a selected angular insertion depth into a computing device executing the techniques of FIG. 7. The computing device may then provide the surgeon with the linear insertion depth needed to position the stimulating assembly at the selected angular insertion depth. For example, a surgeon could enter an indication that the selected angular insertion depth is 360 degrees. The computing device could use the cochlea size measurement to determine that the proper linear insertion depth is 22 mm. The computing device could then inform the surgeon of the calculated linear insertion depth (e.g., output the text: "Insert to 22 mm").

The embodiments of FIG. 7 are an improvement over conventional methods that require pre-operative imaging to manually estimate the largest distance 680 from the cochlea opening 651 to the lateral wall 681 of the cochlea 630. Such estimates, although performed by trained technicians, may be subject to significant variability (e.g., different technicians may use different reference points, etc.). An incorrect pre-operative estimate may result in a failure to achieve a correct angular insertion depth.

Figure 8:
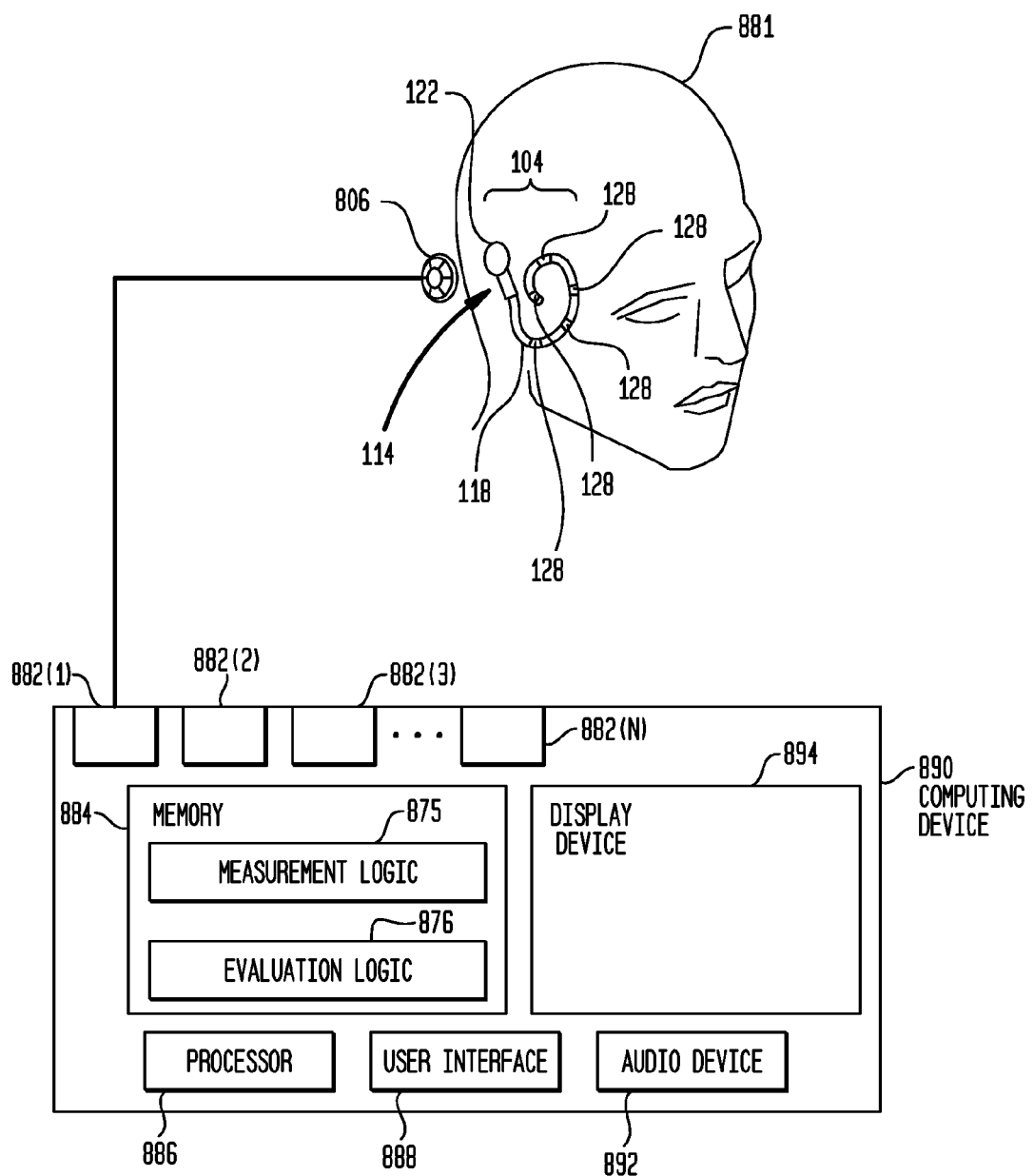
FIG. 8 is a block diagram of a computing device configured to implement intra-operative methods in accordance with embodiments presented herein.

FIG. 8 is a block diagram of an arrangement for implementation of the intra-operative angular insertion depth setting techniques in accordance with embodiments of the present invention. For ease of reference, the embodiment of FIG. 8 will be described with reference to the implantation of implantable component 104 of FIG. 1 into a recipient 891.

In the example of FIG. 8, the angular insertion depth setting functionality is implemented as part of computing device 890. The computing device 890 comprises a plurality of interfaces/ports 882(1)-882(N), a memory 884, a processor 886, a user interface 888, a display device (e.g., screen) 894, and an audio device (e.g., speaker) 892. The memory 884 comprises measurement logic 875 and evaluation logic 876.

The interfaces 882(1)-882(N) may comprise, for example, any combination of network ports (e.g., Ethernet ports), wireless network interfaces, Universal Serial Bus (USB) ports, Institute of Electrical and Electronics Engineers (IEEE) 1394 interfaces, PS/2 ports, etc. In the example of FIG. 8, interface 882(1) is connected to an external coil 806 and/or an external device (not shown) in communication with the external coil. Interface 678(1) may be configured to communicate with the external coil 806 (or other device) via a wired or wireless connection (e.g., telemetry, Bluetooth, etc.). The external 806 may be part of an external component of a cochlear implant.

Memory 884 may comprise read only memory (ROM), random access memory (RAM), magnetic disk storage media devices, optical storage media devices, flash memory devices, electrical, optical, or other physical/tangible memory storage devices. The processor 886 is, for example, a microprocessor or microcontroller that executes instructions for the measurement logic 875 and evaluation logic 876. Thus, in general, the memory 884 may comprise one or more tangible (non-transitory) computer readable storage media (e.g., a memory device) encoded with software comprising computer executable instructions and when the software is executed (by processor 886) it is operable to perform the operations described herein. More specifically, in one embodiment, the measurement logic 875 may be executed by the processor 886 to generate signals/commands that cause stimulator unit 120 to: (1) generate bipolar stimulation, and (2) obtain electrical measurements at one or more contacts. Evaluation logic 876 may be executed by the processor 886 to evaluate the electrical measurements to determine the relative proximity of different contacts and determine the real-time insertion depth of the stimulating assembly 118 and generate appropriate feedback to the surgeon or other user.

In another embodiment, the measurement logic 875 may be executed by the processor 886 to determine when the distal end 250 of stimulating assembly 118 is located at the distal end of the basal region of the recipient's cochlea. The evaluation logic 876 may be executed by the processor 886 to: (1) calculate the length of the basal region of the recipient's cochlea, (2) determine a size of the recipient's cochlea, (3) determine a linear insertion depth for stimulating assembly 118 to achieve a selected angular insertion depth, and (4) generate appropriate feedback to the surgeon or other user.

The computing device 890 may be any of a number of different hardware platforms configured to perform the monitoring techniques presented herein. In one embodiment, the computing device 890 is a computer (e.g., laptop computer, desktop computer, etc.) present within the operating theatre. In another embodiment, the computing device 890 is an intra-operative remote assistant. In a further embodiment, the computing device 890 is an off-the-shelf device, such as a mobile phone or tablet device, to which the measurement logic 875 and evaluation logic 876 is downloaded as an application or program. In these various embodiments of FIG. 8, both control of the measurements and the display/notification of evaluation results occur through the computing device 890.

It is to be appreciated that this software implementation of FIG. 8 is merely illustrative, and that other implementations are possible. For example, in an alternative arrangement, measurement logic 875 and evaluation logic 876 may be implemented fully or partially as hardware elements, such as digital logic gates in one or more application-specific integrated circuits (ASICs).

FIG. 8 illustrates an example in which the monitoring functionality is part of an external computing device. In alternative arrangements, the monitoring functionality may be incorporated, for example, in an external or implantable component of a cochlear implant.

Figure 9:
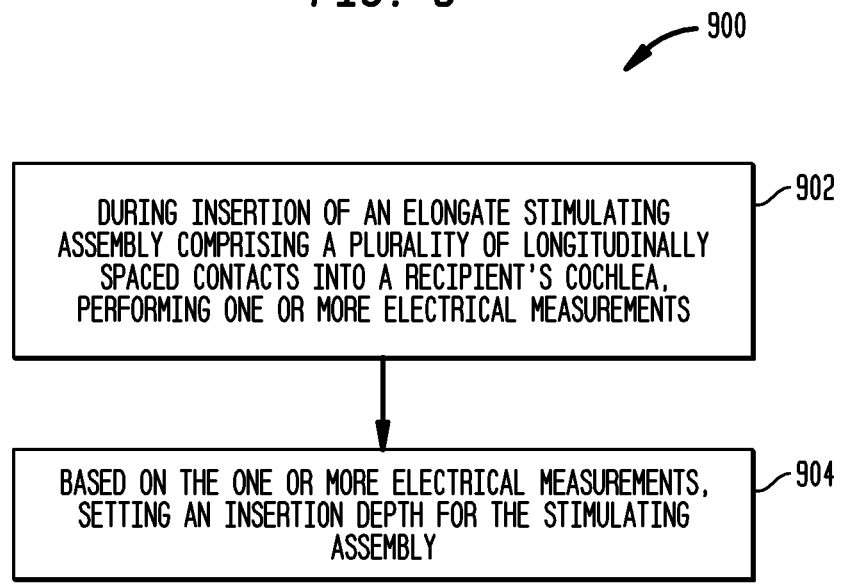
FIG. 9 is a high-level flowchart of a method in accordance with embodiments presented herein.

FIG. 9 is a flowchart of a method 900 in accordance with embodiments presented herein. Method 900 begins at 902 where, during insertion of an elongate stimulating assembly comprising a plurality of longitudinally spaced contacts into a recipient's cochlea, one or more electrical measurements are performed. At 904, based on the one or more electrical measurements, an insertion depth for the stimulating assembly is set.

In accordance with certain embodiments, setting an insertion depth for the distal end of the stimulating assembly comprises determining a real-time angular insertion depth of the distal end of the stimulating assembly within the cochlea. More particularly, one or more bipolar impedance measurements may be performed between a first stimulating contact and one or more other contacts. The one or more bipolar impedance measurements may be evaluated relative to one another to determine physical proximity between the first stimulating contact and the one or more other contacts. The real-time angular insertion depth may be determined based on the physical proximity between the first stimulating contact and the one or more other contacts.

In accordance with further embodiments, setting an insertion depth for the distal end of the stimulating assembly comprises determining a linear insertion depth of the stimulating assembly that corresponds to a selected angular insertion depth of the stimulating assembly. More particularly, at least one electrical measurement is performed to measure a length of a basal region of the cochlea. Based on the measured length of the basal region, a size of the cochlea is calculated and the calculated size of the cochlea is used to determine the linear insertion depth of the stimulating assembly to obtain the selected angular insertion depth for the distal end of the stimulating assembly.

The above examples utilize different intra-cochlea impedance and/or voltage measurements to determine, for example, proximity between pairs of stimulating contacts or proximity of one or more stimulating contacts to the basal wall of a recipient's cochlea. In accordance with embodiments presented herein, these and other intra-cochlea measurements may make use of different frequencies so as to enhance the effectiveness of the measurements.

More specifically, it has been determined that different cochlea structures react differently to different frequencies of stimulation. For example, cochlea tissue (i.e., the cochlea structures) has an impedance which decreases as the frequency is raised to the power of about 0.3 to 0.5. (i.e., its impedance decreases roughly as the square or cube root of the frequency). In the frequencies of interest to cochlear implants, perilymph is generally resistive (Ohmic) in nature, but tissue walls are capacitive in nature. Therefore, as the frequency of the stimulation increases, the impedance of the "capacitive" cells of the tissue decreases and the overall tissue impedance decreases.

This property of tissue is useful for systems that use impedance and voltage sensing measurements. In particular, impedance measured using high frequency stimulation is lower than impedance measured using low frequency stimulation. This means that the tissue appears more "transparent" to the stimulation (electrical current) at high frequencies, when compared to measurements made at low frequencies. Stated differently, in the case of a constant current stimulator, impedances/voltages measured at the end of short pulse widths (i.e., high frequency stimulation) are lower than impedances/voltages measured at the end of long pulse widths (i.e., low frequency stimulation).

For example, referring to the examples of FIGS. 3, 4, and 5, the angular insertion depth is monitored using dipoles created between stimulating contacts located near the distal tip of the stimulating assembly and stimulating contacts located near the proximal end of the stimulating assembly. The impedances/voltages measured from the dipoles are used to determine the angle of insertion of the stimulating assembly. In these examples, the stimulation passes through the modiolus of the recipient's cochlea, particularly when the stimulating assembly is inserted a full turn or more. If these measurements are performed at high frequencies (i.e., by measuring at the end of constant current pulses having a short pulse widths/time lengths), the dipole will be more easily sensed by the basal contacts than if low frequencies (i.e., by measuring at the end of constant current pulses having long pulse widths/time lengths) are used. Since it is desirable to sense the dipole with as large a signal as possible, the high frequency measurements would be advantageous.

In other examples, such as in FIGS. 6 and 7, the proximity of one or more stimulating contacts to, for example, a cochlea wall is determined. In these examples, it is desirable for the impedance of the tissue of the cochlea wall to appear as high as possible so that when a selected stimulating contact approaches the wall, the impedance increases substantially. A measurement system in this case would preferably use a low frequency (long pulse width) measurement as this would increase the impedance of the cochlea wall relative to that of the perilymph and, accordingly, accentuate the increase in impedance when the selected stimulating contact is closer to the wall.

It is to be appreciated that the above embodiments are not mutually exclusive and may be combined with one another in various arrangements.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method, comprising:
   during insertion of an elongate stimulating assembly comprising a plurality of longitudinally spaced contacts into a recipient's cochlea, performing one or more electrical measurements; and
   based on the one or more electrical measurements, setting an angular position of the distal end of the stimulating assembly.

2. The method of claim 1, wherein setting an angular position of the distal end of the stimulating assembly comprises:
   determining a real-time angular position of the distal end of the stimulating assembly within the cochlea.

3. The method of claim 2, further comprising:
   performing bipolar impedance measurements between a first stimulating contact and one or more other contacts;
   evaluating the one or more bipolar impedance measurements relative to one another to determine physical proximity between the first stimulating contact and the one or more other contacts; and
   determining the real-time angular position based on the physical proximity between the first stimulating contact and the one or more other contacts.

4. The method of claim 3, wherein performing bipolar impedance measurements between the first stimulating contact and the one or more other stimulating contacts comprises:
   sequentially delivering stimulation between the first stimulating contact and each of a plurality of other stimulating contacts in a bipolar manner; and
   measuring an impedance between the first stimulating contact and each of the plurality of other stimulating contacts.

5. The method of claim 2, further comprising:
   generating feedback to a user that indicates the real-time angular position of the distal end of the stimulating assembly.

6. The method of claim 1, wherein setting an angular position of the distal end of the stimulating assembly comprises:
   determining a linear insertion depth of the stimulating assembly that corresponds to a selected angular insertion depth of the stimulating assembly.

7. The method of claim 6, further comprising:
   performing at least one electrical measurement to measure a length of a basal region of the cochlea;
   calculating, based on measured length of the basal region, a size of the cochlea; and
   based on the calculated size of the cochlea, determining the linear insertion depth of the stimulating assembly to obtain the selected angular insertion depth for the stimulating assembly.

8. The method of claim 7, wherein performing the at least one electrical measurement comprises:
   performing an impedance measurement to determine when the distal end of the stimulating assembly is in proximity to a beginning of a first turn of the cochlea.

9. The method of claim 6, further comprising:
   generating feedback to a user that indicates the linear insertion depth of the stimulating assembly that corresponds to the selected angular insertion depth of the stimulating assembly.

10. A system, comprising:
    a cochlear implant comprising:
       an implantable stimulator unit, and
       an elongate stimulating assembly comprising a plurality of longitudinally spaced contacts configured to be inserted into a recipient's cochlea; and
    a processor configured to:
       during insertion of the stimulating assembly into the cochlea, perform one or more electrical measurements, and
       based on the one or more electrical measurements, set an angular insertion depth for the stimulating assembly.

11. The system of claim 10, wherein to set an insertion depth for the stimulating assembly, the processor is configured to:
    determine a real-time angular position of the distal end of the stimulating assembly within the cochlea.

12. The system of claim 11, wherein the processor is further configured to:
    perform bipolar impedance measurements between a first stimulating contact and one or more other contacts;
    evaluate the one or more bipolar impedance measurements relative to one another to determine physical proximity between the first stimulating contact and the one or more other contacts; and
    determine the real-time angular position based on the physical proximity between the first stimulating contact and the one or more other contacts.

13. The system of claim 12, wherein to perform the bipolar impedance measurements between the first stimulating contact and the one or more other stimulating contacts, the processor is configured to:
    instruct the stimulator unit to sequentially deliver stimulation between the first stimulating contact and each of a plurality of other stimulating contacts in a bipolar manner; and
    measure an impedance between the first stimulating contact and each of the plurality of other stimulating contacts.

14. The system of claim 11, wherein the processor is further configured to:
    generate feedback to a user that indicates the real-time angular position of the distal end of the stimulating assembly.

15. The system of claim 10, wherein to set an angular insertion depth for the distal end of the stimulating assembly, the processor is configured to:
    determining a linear insertion depth of the stimulating assembly that corresponds to a selected angular insertion depth of the stimulating assembly.

16. The system of claim 15, wherein the processor is configured to:
    perform at least one electrical measurement to measure a length of a basal region of the cochlea;
    calculate, based on measured length of the basal region, a size of the cochlea; and
    based on the calculated size of the cochlea, determine the linear insertion depth of the stimulating assembly that correspond to the selected angular insertion depth of the stimulating assembly.

17. The system of claim 16, wherein to perform the at least one electrical measurement, the processor is configured to:
    perform an impedance measurement to determine when a distal end of the stimulating assembly is in proximity to a beginning of a basal turn of the cochlea.

18. The system of claim 15, wherein the processor is configured to:
    generate feedback to a user that indicates the linear insertion depth of the stimulating assembly that corresponds to a selected angular insertion depth of the stimulating assembly.

19. A method, comprising:
    while inserting a stimulating assembly into the cochlea of a recipient, performing a plurality of electrical measurements between two or more contacts; and
    evaluating the electrical measurements relative to one another to determine a real-time angular position of the stimulating assembly.

20. The method of claim 19, wherein performing a plurality of electrical measurements between two or more contacts comprises:
performing a plurality of impedance measurements between the two or more contacts.

21. The method of claim 19, wherein performing a plurality of electrical measurements between two or more contacts comprises:
performing repeated impedance measurements between a stimulating contact and a selected return contact over a period of time.

22. The method of claim 19, wherein performing a plurality of electrical measurements between two or more contacts comprises:
performing impedance measurements between a stimulating contact and each of a plurality of return contacts while the stimulating assembly is at a first location within the cochlea.

23. A method, comprising:
while inserting a stimulating assembly into the cochlea of a recipient, measuring a length of a basal region of the cochlea;
calculating, based on measured length of the basal region, a size of the cochlea; and
based on the calculated size of the cochlea, determining a linear insertion depth of the stimulating assembly that corresponds to a selected angular insertion depth of the stimulating assembly.

24. The method of claim 23, wherein measuring a length of a basal region of the cochlea comprises:
determining when a distal end of the stimulating assembly is positioned at an end of the basal region of the cochlea; and
measuring the length of the basal region of the cochlea from the linear insertion length of the stimulating assembly when the distal end of the stimulating assembly is positioned at the end of the basal region of the cochlea.

25. The method of claim 24, wherein determining when the distal end of the stimulating assembly is positioned at the end of the basal region of the cochlea comprises:
performing an impedance measurement to detect when the distal end of the stimulating assembly is adjacent to a wall of the cochlea at the distal end of the basal region.

26. The method of claim 24, wherein the distal end of the stimulating assembly includes a pressure sensor, and wherein determining when the distal end of the stimulating assembly is positioned at the end of the basal region of the cochlea comprises:
detecting, with the pressure sensor, when the distal end of the stimulating assembly contacts the wall of the cochlea at the distal end of the basal region.

* * * * *